(12) United States Patent
Maejima et al.

(10) Patent No.: US 7,718,797 B2
(45) Date of Patent: May 18, 2010

(54) FASUDIL-CONTAINING PREPARATION AND METHOD OF IMPROVING STABILITY THEREOF

(75) Inventors: Takuji Maejima, Shizuoka (JP); Miki Ohshima, Shizuoka (JP)

(73) Assignee: Asahi Kasei Pharma Corporation, Tokyo (JP)

( * ) Notice: Subject to any disclaimer, the term of this patent is extended or adjusted under 35 U.S.C. 154(b) by 920 days.

(21) Appl. No.: 10/598,303

(22) PCT Filed: Mar. 4, 2005

(86) PCT No.: PCT/JP2005/003772

§ 371 (c)(1),
(2), (4) Date: Aug. 24, 2006

(87) PCT Pub. No.: WO2005/087237

PCT Pub. Date: Sep. 22, 2005

(65) Prior Publication Data

US 2008/0234483 A1    Sep. 25, 2008

(30) Foreign Application Priority Data

Mar. 16, 2004    (JP) .............................. 2004-075031

(51) Int. Cl.
*A61P 25/00* (2006.01)
*A61P 9/10* (2006.01)
*A61K 9/08* (2006.01)
*A61K 31/551* (2006.01)
*C07D 403/12* (2006.01)

(52) U.S. Cl. .................................................. 540/575

(58) Field of Classification Search ................. 540/575
See application file for complete search history.

(56) References Cited

U.S. PATENT DOCUMENTS 4,678,783 A    7/1987    Hidaka et al.

5,403,412 A    4/1995    Hidaka et al.

FOREIGN PATENT DOCUMENTS

| CA | 2248794 | 5/2004 |
|---|---|---|
| CN | 1215334 | 4/1999 |
| EP | 0845265 | 6/1998 |
| EP | 0870767 | 10/1998 |
| JP | 61-227581 | 10/1986 |
| JP | 5-3851 | 1/1993 |
| JP | 9-024085 | 1/1997 |
| JP | 11-292787 | 10/1999 |
| WO | 97/02260 | 1/1997 |
| WO | 97/23222 | 7/1997 |

OTHER PUBLICATIONS

Asahi Kasei, financial report for fiscal 2004, May 10, 2005.*
English language abstract of JP 9-24085, 1997.
Asahi Kasei Pharma Products Information from 2003 for the Eril injection preparation (Oct. 2003 revision; 6th edition); accompanied by an English language translation thereof.
Asahi Kasei Pharma Products Information from 2003, showing photos of Asahi Kasei Pharma Products; accompanied by English language translation thereof.
"Interview Form" for Eril, a document in which Eril is described in detail; document is prepared by pharmaceutical manufacturer upon request of Japan Hospital Pharmaceutical Association and is considered a comprehensive manual for such pharmaceutical; accompanied by an English language translation of pp. 3-7, 2003.

* cited by examiner

*Primary Examiner*—Brenda L Coleman
(74) *Attorney, Agent, or Firm*—Greenblum & Bernstein, P.L.C.

(57) ABSTRACT

Fasudil-containing preparations that despite the us of a container excelling in the visibility of contents without particularly blocking of light, exhibit high stability against light; and a method of improving the stability of the preparations against light of storing the same. By regulating the pH value of aqueous solution of fasudil charged in a colorless transparent container to ≦5.5, there can be provided fasudil-containing preparations excelling in stability against light; and can be provided a method of improving the stability of the aqueous solution of fasudil against light, or storing the same.

17 Claims, No Drawings

FASUDIL-CONTAINING PREPARATION AND METHOD OF IMPROVING STABILITY THEREOF

This application is a national stage entry under 35 U.S.C. §371 of PCT/JP05/03772, filed Mar. 4, 2005.

TECHNICAL FIELD

The present invention relates to a fasudil hydrochloride-containing preparation with an excellent stability against light, a method for improving the stability of this preparation against light, and a method for preserving an aqueous solution of fasudil-hydrochloride in a transparent container.

BACKGROUND ART 1-(5-Isoquinolinesulfonyl)homopiperazine hydrochloride (hereinafter referred to as "fasudil hydrochloride") having an excellent vasodilatation effect is commercially available under the trademark of "Eril Inj." (manufactured by Asahi Kasei Pharma Corp.) and clinically used as an injection preparation for improving cerebrovascular spasm after a subarachnoid bleeding operation and an accompanying brain ischemia symptom (Patent Document 1).

Fasudil hydrochloride crystals are known to include crystals not containing crystal water (hereinafter referred to as "fasudil hydrochloride anhydride") and crystals containing crystal water (hereinafter referred to as "fasudil hydrochloride hydrate") (Patent Document 2).

An aqueous solution of fasudil hydrochloride is known to produce decomposition products by irradiation of light. To reduce generation of the decomposition products by light irradiation, injections and the like containing an aqueous solution of fasudil hydrochloride are supplied to the market in a form shielded from light, e.g. filled into a brown container or the like.

An aqueous solution injection of fasudil hydrochloride filled into a colored container or a container coated with a light-shielding coating of which the transmission rate of tight particularly with a wavelength of 350 nm is 10% or less has been known (Parent Document 3).

[Patent Document 1] JP-B5-3851

[Patent Document 2] WO 97/02260

[Patent Document 3] JP-A-9-24085

DISCLOSURE OF THE INVENTION

Problems to be Solved by the Invention

A conventional technique of using colored containers and the like is not satisfactory from the viewpoint of detecting insoluble foreign matter and inspecting the outward appearance, since it is difficult to identify the state of the medical fluid contained therein. An object of the present invention is to provide a fasudil hydrochloride-containing preparation with excellent stability against light, a method for improving the stability of this preparation against light, and a method for preserving the fasudil-hydrochloride preparation by using a container with excellent visibility of the contents without specifically shielding light as in the case of prior art technologies.

Means for the Solution of the Problems

As a result of extensive studies to achieve the above object, the present inventor have found that formation of decomposed materials due to light irradiation can be suppressed, coloration can be prevented, and stability against light is improved unexpectedly by reducing the pH of the fasudil-hydrochloride aqueous solution.

Specifically, the present invention provides the following items.

[1] A method for improving photostability of fasudil or a salt thereof in a transparent and colorless container comprising maintaining an aqueous solution of the fasudil or salt thereof at a pH of 5.5 or less.

[2] The method according to [1] comprising maintaining the aqueous solution of the fasudil or salt thereof at a pH of 5 or less.

[3] The method according to [1] or [2], wherein the photostability improvement comprises reducing the content of decomposition products of fasudil and/or preventing coloration.

[4] The method according to any one of [1] to [3], wherein the aqueous solution of the fasudil or salt thereof is an intravascular injection preparation.

[5] The method according to any one of [1] to [4] wherein the transparent and colorless container is a transparent and colorless class container.

[6] A method for preserving an aqueous solution of fasudil or a salt thereof in a transparent and colorless container comprising maintaining the aqueous solution at a pH of 5.5 or less.

[7] The method according to [6] comprising maintaining the aqueous solution of the fasudil or salt thereof at a pH of 5 or less.

[8] The method according to [6] or [7], wherein the aqueous solution of the fasudil or salt thereof is an intravascular injection preparation.

[9] The method according to any one of [6], [7], and [8], wherein the transparent and colorless container is a transparent and colorless glass container.

[10] An injection fluid preparation comprising an aqueous solution of fasudil or a salt thereof at a pH of 5.5 or less aseptically filled in a transparent and colorless container.

[11] The injection fluid preparation according to [10], wherein the aqueous solution of the fasudil or salt thereof has a pH of 5 or less.

[12] The injection fluid preparation according to [10] or [11], wherein the aqueous solution of the fasudil or salt thereof is an intravascular injection preparation.

[13] The injection fluid preparation according to any one of [10], [11], and [12] wherein the transparent and colorless container is a transparent and colorless glass container.

In addition, the present invention may include the following inventions (1) A fasudil hydrochloride-containing preparation comprising an aqueous solution of fasudil hydrochloride filled into a transparent and colorless container, wherein 95% or more of the fasudil hydrochloride remains after irradiation by light of 600,000 Lux-hr using a D65 lamp.

(2) The fasudil hydrochloride-containing preparation according to (1), wherein the aqueous solution of the fasudil hydrochloride has a pH of 7.5 or less.

(3) A fasudil hydrochloride-containing preparation comprising an aqueous solution of fasudil hydrochloride filled into a transparent and colorless container, wherein the fasudil hydrochloride aqueous solution has a pH of 7.5 or less.

(4) A method for improving stability of fasudil hydrochloride against irradiation by light of 600,000 Lux-hr using a D65 lamp, comprising maintaining an aqueous solution of fasudil hydrochloride at a pH of 1.5 or less.

(5) A method for presenting an aqueous solution of fasudil hydrochloride in a transparent and colorless container, comprising maintaining the aqueous solution at a pH of 7.5 or less.

EFFECT OF THE INVENTION

According to the present invention, a fasudil-containing preparation comprising an aqueous solution of fasudil or a salt thereof (particularly preferably fasudil hydrochloride) with improved photostability and excellent visibility of the content can be provided.

The preparation of the present invention, which responds to the requirements for suppressing formation of decomposition products of medical supplies to the maximum extent in this manner, has a long shelf life with a consequence of cost reduction.

A brown container is expensive as compared with a transparent and colorless container. In addition, when a brown container is used, not only it is difficult to identify the state of medical fluid in the container, but also the detection accuracy of foreign insoluble matter decreases on the occasion of automatic inspection of the content by image processing using a camera. According to the present invention, in which a brown container need not be used, high quality preparations can be consistently supplied in a stable manner at a reduced cost, while rejecting products containing foreign insoluble matter without fail.

BEST MODE FOR CARRYING OUT THE INVENTION

The present invention will now be described in more detail.

In the present invention, fasudil or a salt thereof is used. Preferred examples of the salts include an acid additional salt. Examples of acids for the acid addition salt include inorganic acids such as hydrochloric acid, hydrobromic acid, phosphoric acid, and sulfuric acid and organic acids such as acetic acid, citric acid, tartaric acid, lactic acid, succinic acid, fumaric acid, maleic acid, and methanesulfonic acid. Further examples of acids include thiocyanic acid, boric acid, formic acid, haloacetic acid, propionic acid, glycolic acid, gluconic acid, malonic acid, anthranilic acid, benzoic acid, cinnamic acid, p-toluenesulfonic acid, alkylbenzenesulfonic acid, naphthalenesulfonic acid, sulfanilic acid. Furthermore, a metal complex may be considered. Examples of metal complexes include a complex with zinc, nickel, cobalt, copper, iron, and the like.

A particularly preferred salt is fasudil hydrochloride. Examples of fasudil hydrochlorides include fasudil hydrochloride anhydride and fasudil hydrochloride hydrate (e.g., ½ hydrate). Either the anhydride or hydrate can be used in the present invention.

A fasudil aqueous solution refers to a solution of fasudil or a salt thereof (particularly preferably fasudil hydrochloride, hereafter the fasudil salts are from time to time referred to as "fasudil hydrochloride") in a liquid of which the major component is water, for example, distilled water for injection, a isotonic sodium chloride solution, a glucose solution, and the like. Although the concentration may be appropriately adjusted, a concentration equivalent to the solubility or less than the solubility of the fasudil or salt thereof is preferred. For example, the upper limit is preferably 250 mg/ml or less, more preferably 200 mg/ml or less, still more preferably 150 mg/ml or less, particularly preferably 100 mg/ml or less, and most preferably 60 mg/ml or less or 40 mg/ml or less. The lower limit is preferably 0.1 m/ml or more, more preferably 1 mg/ml or more, still more preferably 5 mg/ml or more, and most preferably 10 mg/ml or more. The above concentrations are indicated as the weight of fasudil hydrochloride ½ hydrate.

In the present invention, a preferred example of the transparent and colorless container includes a container having light transmission rate with a wavelength of 450 nm of 45% or more. The transmission rate of the container is preferably 50% or more, and more preferably 55% or more. The contents of the container are easily visible if the transmission rate of light with a wavelength of 450 nm is 45% or more. Visibility, which indicates ease of observing, the fluid in the container from the outside, can be confirmed by, for example, a method of adding water-insoluble fine particles to the container and counting the period of time required for identifying the particles.

Specific examples of the transparent and colorless container used in the present invention include an ampoule made of transparent and colorless glass (volume: 2 ml, light transmission with a wavelength of 450 nm: 90.4% (manufactured by Murase Glass Co., Ltd.)), a vial made of transparent and colorless glass (volume: 30 ml, light transmission with a wavelength of 450 nm: 92.0% (manufactured by Fuji Glass Co., Ltd.)), and a vial made of a transparent and colorless resin (volume: 10 ml, light transmission with a wavelength of 450 nm: 91.5% (manufactured by Daikyo Seiko, Ltd.)). The light transmission of a transparent and colorless container can be measured using, for example, a spectrophotometer "UV-2500PC" manufactured by Shimadzu Corp. Assuming the absorbance measured when a cell holder is empty as 100% transmission, the percent transmission can be determined by measuring the absorbance of the material of the container or package by cutting a sample of about 0.9×4 cm and placing it in the same cell holder. The values of the wavelength and transmission rate respectively include ±0.5% of measurement error allowance.

Light irradiation of 600,000 Lux-hr includes, for example, irradiation of light at 5000 Lux for 120 hours. As the D65 lamp, "FLR20S•D-EDL-D65/M NA" manufactured by TOSHIBA Corp. is preferably used.

In order to adjust the aqueous solution of fasudil or a salt thereof (e.g. fasudil hydrochloride) to 7.5 pH or less (or less than 7.5 pH or 7 pH or less), a pH-adjusting agent, a pH-buffering agent, or the like is used to adjust the solution to the desired pH. The pH of the aqueous solution of the present invention is preferably 5.5 or less, more preferably 5.0 or less, particularly preferably 4.0 or less, and most preferably 3.0 or less, for example. Other preferred examples of pH ranges include 4.5 or less, 3.5 or less, and 2.0 or less.

Examples of pH-adjusting agents that can be used include hydrochloric acid, sodium citrate, sodium dihydrogencitrate, succinic acid, glacial acetic acid, ammonium acetate, sodium acetate, sodium hydrogencarbonate, triethanolamine, lactic acid, sodium lactate solution, meglumine, monoethanolamine, aluminum potassium sulfate, sodium monohydrogenphosphate, trisodium phosphate, dipotassium phosphate, potassium dihydrogenphosphate, sulfuric acid, phosphoric acid, citric acid, sodium dihydrogenphosphate, sodium hydrogenphosphate, sodium carbonate, and sodium hydroxide. Preferred pH-adjusting agents are hydrochloric acid and sodium hydroxide. Other pH-adjusting agents that can be used include adipic acid, aqueous ammonia, glucono-δ-lactone, gluconic acid, diisopropanolamine, tartaric acid, D-tartaric acid, sodium L-tartrate, calcium hydroxide, magnesium hydroxide, triisopropanolamine, carbon dioxide, calcium lactate, monosodium fumarate, sodium propionate, boric acid, ammonium borate, borax, maleic acid, dl-malic acid, acetic acid, potassium hydroxide, and the like.

As a pH-buffering agent any pharmaceutically acceptable solutions exhibiting a pH buffering action can be used. For example, a buffer composition of the buffering agent can be appropriately selected from acetic acid, citric acid, succinic acid, tartaric acid, phosphoric acid, lactic acid, and their salts.

In the fasudil-containing preparation comprising an aqueous solution of fasudil or a salt thereof (e.g. fasudil hydrochloride) aseptically filled in a transparent and colorless container, the amount of the fasudil or salt thereof remaining after irradiation of 600,000 Lux-hr using a D65 lamp is preferably 95% or more, more preferably 96% or more or 97% or more, and particularly preferably 97.5% or more or 98% or more. The content of decomposition products (the area percentage of decomposition products in HPLC) is preferably 5% or less, more preferably 4% or less or 3% or less, and particularly preferably about 2.5% or less or 2.0% or less.

The fasudil-containing preparation is supplied to the market filled into a container such as an ampoule, a vial, a syringe, a soft bag, or the like. The material for containers such as a vial, syringe, and soft bag includes a transparent material. Appropriate materials are selected from glass; plastics such as polypropylene, polyethylene, cyclic polyolefin, a copolymer of cyclic polyolefin and α-olefin, polyethylene terephthalate, polystyrene, ABS resin, polymethylpentene, hexafluoro resin, polymethyl methacrylate, and polycarbonate; metals such as stainless steel, gold, aluminum, aluminum alloy, and titanium; ceramics; complex materials such as carbon composite materials; and quartz, preferably from glass and plastics. Glass is a particularly preferred material.

To the extent that transparence can be maintained, the container used may be coated or covered with a coating, film, or the like.

The inner surface of glass may not be treated or may be treated by any treatment that can maintain transparency, for example, by silicon treatment, sulfur treatment, silicon-sulfur treatment, or the like.

The surface of the rubber stopper used for the container such as a vial and soft bag may be treated by silicon or coated with a fluororesin, if required.

The content of fasudil or a salt thereof (e.g. fasudil hydrochloride) may be appropriately adjusted as required.

Examples of the form of fasudil or a salt thereof (e.g. fasudil hydrochloride) to be filled into containers include an aqueous solution preparation. As required, an isotonic agent such as a salt (e.g. sodium chloride) or a saccharide (e.g. glucose), a soothing agent such as phenol, and the like that do not affect the properties of the fasudil or salt thereof (e.g. fasudil hydrochloride) can be added. More specifically, examples of isotonic agents include aminoethylsulfonic acid, sodium hydrogensulfite, sodium chloride, benzalkonium chloride, magnesium chloride, fructose, xylitol, citric acid, sodium citrate, glycerin, calcium bromide, sodium bromide, sodium hydroxide, D-sorbitol, sodium hydrogencarbonate, nicotinic acid amide, sodium lactate solution, glucose, propylene glycol, benzyl alcohol, macrogol 4000, D-mannitol, anhydrous sodium pyrophosphate, phosphoric acid, sodium hydrogenphosphate, potassium dihydrogenphosphate, sodium dihydrogenphosphate, and the like. Further examples of isotonic agents include potassium chloride, calcium chloride, boric acid, and borax. Examples of antioxidants include ascorbic acid, sodium hydrogensulfite, sodium sulfite, α-thioglycerol, sodium edetate, cysteine hydrochloride, citric acid, sodium thioglycolate, sodium thiomalate, sodium pyrosulfite, and butylhydroxyanisol. Further examples of antioxidants include sodium nitrite, L-ascorbyl stearate, erythorbic acid, tocopherol acetate, potassium dichloroisocyanurate, dibutylhydroxytoluene, 2,6-di-t-butyl-4-methylphenol, soybean lecithin, Tenox 2, natural vitamin E, tocopherol, d-δ-tocopherol, ascorbyl palmitate, 1,3-butylene glycol, pentaerythrityl tetrakispropionate, propyl gallate, 2-mercaptobenzimidazole, oxyquinoline sulfate, and the like. Examples of soothing agents include inositol, creatinine, chlorobutanol, sodium hydrogencarbonate, glucose, propylene glycol, benzyl alcohol, magnesium sulfate, and the like. Further examples of soothing agents include ethyl aminobenzoate, phenol, and the like.

When an aqueous solution of the fasudil or salt thereof (e.g. fasudil hydrochloride) is filled into a container, the amount may be appropriately adjusted according to the volume of the container. In general, such an amount is 100% or less, preferably 99% or less, more preferably 95% or less, and most preferably 90% or less, but 30% or more, preferably 40% or more, and more preferably 50% or more of the maximum volume of the container.

The administration routes of fasudil include oral administration, intraarterial injection, intravenous injection, subcutaneous injection, intracutaneous injection, intramuscular injection, drip intravenous infusion, and the like. Among these administration routes, intravascular injection is preferred, with drip intravenous infusion and intravenous injection being particularly preferred. As the form of the preparation, injection preparations including an injection preparation for blood vessel application is preferable.

Stimulus to the body is anticipated when the injection preparation of the present invention has a low pH. In such a case, the injection preparation is preferably diluted with an electrolyte solution or a glucose solution to increase the pH before use. For example, to prepare an injection preparation containing 30 mg, of the fasudil or salt thereof, a preparation containing a Small amount (30 m/l ml or 30 mg/2 ml) is provided, which is diluted with 50 to 500 ml of an electrolyte solution or a glucose solution before use. The upper volume limit of the injection preparation is preferably 50 ml or less, more preferably 30 ml or less, particularly preferably 10 ml or less, and most preferably 2 ml or less. The lower volume limit is preferably 0.5 ml or more, more preferably 0.75 ml or more, and particularly preferably 1 ml or more.

The present invention will now be described in detail by way of examples, which should not be construed as limiting the present invention.

EXAMPLES

Reference Preparation Example

Homopiperazine (3.413 g) was dissolved in tetrahydrofuran (57 ml) with stirring. After cooling the solution to −5° C., 5-isoquinolinesulfonyl chloride hydrochloride (3.00 g) was added while maintaining the internal temperature at 10° C. or less. The mixture was stirred at 5° C. or less for four hours. The reaction mixture was allowed to stand to reach room temperature and filtered to remove insoluble matter. The filtrate was concentrated under reduced pressure, followed by the addition of ethyl acetate (57 ml), water (17 ml), and 3 N hydrochloric acid aqueous solution (6.4 ml). The mixture was separated into layers to obtain a water layer. After washing the water layer with ethyl acetate (7 ml), water (6 ml), ethyl acetate (57 ml), and 6 N sodium hydroxide aqueous solution (3 ml) were added to separate the mixture into layers and obtain an organic layer. The organic layer was concentrated under reduced pressure and the residue was dried under reduced pressure to obtain fasudil (1.36 g). The yield was 41%. The fasudil is processed by the method described in JP-A-9-71582 to obtain fasudil hydrochloride.

Fasudil can also be obtained in the same manner using the solvents listed below instead of tetrahydrofuran used in the Reference Preparation Example at yields described in the parentheses. Acetone (22%), acetonitrile (30%), 1,2-dimethoxyethane (31%), 2-butanone (24%), anisole (34%), isopropyl ether (10%), ethyl acetate (38%), toluene (18%), etc. Concentration of the filtrate was unnecessary when anisole, isopropyl ether, ethyl acetate, and toluene were used as the solvent.

<Method for Preparing Fasudil-Containing Preparations with Various pHs>

Fasudil-hydrochloride ½ hydrate (3.08 g) and sodium chloride (0.8 g, manufactured by Wako Pure Chemical Industries, Ltd.) were dissolved in water (80 ml). After adjusting the pH of all solutions to 1, 2, 3, 4, 5, 6, 7, 7.5, 8, and 9 by addition of a diluted hydrochloric acid or sodium hydroxide reagent solution, the volume of each solution was adjusted to 100 ml by addition of water. The fasudil hydrochloride aqueous solutions were aseptically filtered and 2 ml of the filtrates were filled in transparent and colorless glass ampoules (2 ml (manufactured by Namicos Corp.)). The ampoules were melt-sealed to obtain fasudil-containing preparations with the pH of 1-9 (hereinafter referred to as "fasudil hydrochloride-containing preparations").

<Measuring Test of Decomposition Product Content>

The ampoules of fasudil hydrochloride-containing preparations with the pH of 1-9 obtained from the above process were placed in a photostability tester "LT-120D3CJ" (manufactured by Nagano Science Co., Ltd.) and irradiated with light at 600,000 Lux-hr from a D65 lamp. The test was carried out under constant conditions at 25±2° C.

After irradiation with light, the transmission of light at a wavelength of 400 nm through the fasudil aqueous solutions was measured using a spectrophotometer "UV-2500PC" (manufactured by Shimadzu Corp.) in order to evaluate the degree of coloration of the solutions. Conditional upon an agreement of the measured transmission rate with the coloration judgment with naked eye observation, the degree of coloration was evaluated by the transmission rate.

The decomposition product content (%) in the above fasudil aqueous solutions was measured by high performance liquid chromatography (HPLC).

The decomposition product content (%) is a peak area ratio (%) measured by HPLC and calculated by dividing the peak area of the decomposition products originating from fasudil by the total peak area of fasudil and the decomposition products originating from fasudil, and multiplying the quotient by 100.

The residual ratio (%) is determined by dividing the peak area of fasudil by the above total peak area and multiplying the quotient by 100. The relationship of [Decomposition product content (%)=100−residual ratio (%)] applies.

Note that the total peak area excludes the peak area of substances not derived from fasudil, such as additives to the preparation.

Peak area ratio (%) of fasudil hydrochloride defined in this specification is a value including ±0.5% of measurement error allowance. The results are shown in Table 1.

(Irradiation Conditions)
Light source: D65 lamp ("FLR20S•D-EDL-D65/M NA" manufactured by TOSHIBA Corp.)
Illuminance: 5000 Lax
Illuminance amount: 600,000 Lux·hr
Instrument: Photostability tester "LT-120D3CJ" (manufactured by Nagano Science Co., Ltd.)
Temperature: 25±2° C.

(Transmission Rate Measuring Conditions of Medical Fluid)
Instrument: Spectrophotometer "UV-2500PC" manufactured by Shimadzu Corp.
Wavelength: 400 nm
Cell: made from quartz
Control fluid: water for injection (HPLC Measurement Conditions)
Column: YMC-Pack CS A-203
Detector: Ultraviolet absorptiometer 215 nm
Mobile phase: 0.3 mol/l ammonium phosphate buffer solution (5.0 pH)/acetonitrile mixture

TABLE 1

| pH | Transmission rate (%) | Decomposition product content (%) (Amount of remaining fasudil) |
|---|---|---|
| 1 | 92.95 | 1.84 (98.16) |
| 2 | 87.75 | 1.77 (98.23) |
| 3 | 70.09 | 2.33 (97.67) |
| 4 | 54.32 | 2.54 (97.46) |
| 5 | 29.25 | 2.77 (97.23) |
| 6 | 13.99 | 2.77 (97.23) |
| 7 | 9.86 | 3.35 (96.65) |
| 7.5 | — | 4.77 (95.23) |
| 8 | — | 6.21 (93.79) |
| 9 | — | 6.61 (93.39) |

As described above, it has been confirmed that the photostability of fasudil hydrochloride aqueous solutions can be improved by lowering the pH, even if the solutions are stored in a transparent and colorless container. In an aqueous solution with a low pH, the decomposition product content was controlled at a low level and die degree of coloration was low. A pH of 5.5 or less of the aqueous solution was confirmed to be preferable, with more preferable pHs being in the order of 5 or less, 4.5 or less, 4 or less, 3.5 or less, 3 or less, 2.5 or less, 2 or less, 1.5 or less, and 1 or less. Fasudil hydrochloride aqueous solutions with a pH of 7.5 or less had a decomposition product content of 5% or less (residual ratio of 95% or more) and exhibited improved photostability as compared with fasudil hydrochloride aqueous solutions with an 8 or greater pH.

INDUSTRIAL APPLICABILITY

According to the present invention, formation of decomposition products in a fasudil aqueous solution preparation due to light can be suppressed, stability of a fasudil aqueous solution is improved, and the solution can preserved stably over a lone period of time.

The invention claimed is:

1. A method for improving photostability of fasudil or a salt thereof in a transparent and colorless container comprising maintaining an aqueous solution of the fasudil or salt thereof at a pH of less than 5.0.

2. The method according to claim 1 comprising maintaining the aqueous solution of the fasudil or salt thereof at a pH of 4.5 or less.

3. The method according to claim 1, wherein the photostability improvement comprises reducing the content of decomposition products of fasudil and/or preventing coloration.

4. The method according to claim 1, wherein the transparent and colorless container is a transparent and colorless glass container.

5. A method for preserving an aqueous solution of fasudil or a salt thereof in a transparent and colorless container comprising maintaining the aqueous solution at a pH of less than 5.0.

6. An injection fluid preparation comprising an aqueous solution of fasudil or a salt thereof at a pH of less than 5.0 aseptically filled in a transparent and colorless container.

7. The method according to claim 2, comprising maintaining the aqueous solution of the fasudil or salt thereof at a pH of 4 or less.

8. The method according to claim 7, comprising maintaining the aqueous solution of the fasudil or salt thereof at a pH of 3.5 or less.

9. The method according to claim 8, comprising maintaining the aqueous solution of the fasudil or salt thereof at a pH of 3 or less.

10. The method according to claim 9, comprising maintaining the aqueous solution of the fasudil or salt thereof at a pH of 2.5 or less.

11. The method according to claim 10, comprising maintaining the aqueous solution of the fasudil or salt thereof at a pH of 2 or less.

12. The method according to claim 11, comprising maintaining the aqueous solution of the fasudil or salt thereof at a pH of 1.5 or less.

13. The method according to claim 12, comprising maintaining the aqueous solution of the fasudil or salt thereof at a pH of 1 or less.

14. The preparation according to claim 6, comprising an aqueous solution of fasudil or a salt thereof at a pH of 2.0 to 4.5, aseptically filled in a transparent and colorless container.

15. The preparation according to claim 6, comprising an aqueous solution of fasudil or a salt thereof at a pH of 1.0 to less than 2.0, aseptically filled in a transparent and colorless container.

16. The method according to claim 5, comprising maintaining the aqueous solution at a pH of 2.0 to 4.5.

17. The method according to claim 5, comprising maintaining the aqueous solution at a pH of 1.0 to less than 2.0.

* * * * *